United States Patent [19]

Morris

[11] Patent Number: 4,889,842
[45] Date of Patent: Dec. 26, 1989

[54] CONCANAVALIN A DIMERS AS THERAPEUTIC AGENTS

[76] Inventor: Randall E. Morris, 1765 Fallen Leaf La., Los Altos, Calif. 94022

[21] Appl. No.: 21,295

[22] Filed: Mar. 3, 1987

[51] Int. Cl.$^4$ .................. A61K 37/10; A01N 1/02
[52] U.S. Cl. .................................... 514/8; 435/1; 514/2
[58] Field of Search .................. 514/8, 2; 435/1

[56] References Cited

PUBLICATIONS

Gunther et al., (1973) Proc. Natl. Acad. Sci. USA, USA 70(4):1012–1016.
Edelman et al., (1973) Proc. Natl. Acad. Sci. USA 70:1442.
Kind et al., (1973) Proc. of the Soc. for Experimental Biology and Medicine 142:680.
Reichert et al., (1973) Nature New Biology 242:146.
Cunningham, (1975) Annals of the New York Acad. of Sci. 234:219.
Wang et al., (1975) Proc. Natl. Acad. Sci. USA 72:1917.
Wang et al., "Concanavalin A as a Tool," edited by H. Bittiger (Wiley Interscience publication, 1976).
Hadden et al., (1976) Proc. Natl. Acad. Sci. USA 73:1717.
Ozato et al., (1976) Journal of Experimental Medicine 143:1.
Bornens et al., (1976) J. Biochem. 65:61.
McClain et al, (1976) Journal of Experimental Medicine 144:1494.
Ozato et al., (1977) Journal of Cellular Physiology 93:153.
Basham et al., (1977) Journal of Immunology 118:863.
Rubens et al., (1977) Journal of Immunology 118:180.
Wang et al., (1978) Journal of Biological Chemistry 253:3000–3007.
Beppu et al., (1979) J. Biochem. 85:1275.
Kataoka et al., (1979) Gann 70:155.
Dobson et al., (1980) Biochem. Biophys. Acta 629:305.
Larner et al., (1980) Molecular & Cellular Biochemistry 32:123.
Blackard et al., (1980) Metabolism 29:691.
Ruud et al., (1981) Scand. J. Immunol. 14:153.
Koppel et al., (1982) Journal of Cell Biology 93:950.
Takahashi et al., (1982) Hepatology 2:249.
Zenian et al., (1982) J. Parisitol. 68:408.
Leak et al., (1984) Journal of Ultrastructure Research 86:1.
Romeo et al., (1978) Membrane Biol. 44:221
Smolen et al., (1980) Infection and Immunity 28:475.
Petty et al., (1981) Cell Biophys. 3:19.
Sheterline et al., (1981) Journal of Cell Biology 90:743.
Siraganian et al., (1975) J. of Immunology 114:886.
Santoro et al., (1983) Biochem. Biophys. Acta. 757:101.
Inoue et al., (1977) Biochim. Biophys. Acta 467:130.
Wise et al., (1978) J. Cell. Sci. 30:63.
Chicken et al., (1983) Biochem. Biophys. Acta 729:200.
Mehta et al., (1983) Biochim. Biophys. Acta. 762:9.
Garrity et al., (1982) Antimicrobial Agents and Chemotherapy 21:450.
Diaz-Maurino et al.–Chem. Abst. vol. 101, (1984) p. 21191g.

*Primary Examiner*—Sam Rosen
*Attorney, Agent, or Firm*—Irell & Manella

[57] ABSTRACT

Homogeneous dimeric forms of concanavalin A, including the dimer form of native concanavalin A and dimeric derivatives of concanavalin A, are effective immunoregulatory agents with a good balance of high activity and low toxicity. Immunoregulatory pharmaceutical materials composed of one or a mixture of such isolated dimeric materials are disclosed as are methods of inducing immunoregulation in mammals by administering to such mammals an effective immunoregulatory amount of such pharmaceutical materials.

9 Claims, No Drawings

CONCANAVALIN A DIMERS AS THERAPEUTIC AGENTS

BACKGROUND OF THE INVENTION

1. Field of the Invention

This invention is in the field of pharmaceutical chemistry and therapeutics. More particularly, it relates to concanavalin A materials having immunoregulatory activity and their use in applications where that activity is called for.

2. Prior Art

Concanavalin A (CA) is a well characterized plant lectin that reacts with numerous cell types and various molecules of the mammalian immune system. The cummulative effect of these reactions is often unpredictable, since CA has been shown both to stimulate and to suppress the immune system in in vitro and in vivo tests. Further complicating an understanding of these diverse biological effects is CA's molecular heterogeneity. Solutions of CA are mixtures of varying proportions of multimolecular aggregates, tetramers, dimers, monomers and free and associated monomer fragments. The exact composition of this mixture is dependent upon the preparation scheme and the type of handling the particular sample has received. H. Markowitz and colleagues reported in SCIENCE, 163, 476, that the CA mixture provided immunosuppressive activity in grafts in mice. R. Weil, III and colleagues reported at TRANSPLANTATION, 17, No. 6 600, (1974) the use of CA to increase rat heart allograft survival.

A variety of CA derivatives are described in the literature. These include succinylated CA, or SCA; acetylated CA or ACA; cross-linked CA; hybrid CA; and the reaction product of CA with maleic anhydride, etc. With any of these materials, there is a need to provide reprodcibility in composition and a need to optimize the desired activity while minimizing side effects and toxicity.

STATEMENT OF THE INVENTION

It has now been found that homogeneous dimeric forms of concanavalin A, including the dimer form of native concanavalin A and dimeric derivatives of concanavalin A, are effective immunoregulatory agents with a good balance of high activity and low toxicity.

In one aspect this invention provides immunoregulatory pharmaceutical materials composed of one or a mixture of such isolated dimeric materials.

In another aspect this invention provides methods of inducing immunoregulation in mammals by administering to such mammals an effective immunoregulatory amount of such pharmaceutical materials.

In a preferred aspect, the invention employs this immunoregulation to treat transplant or graft rejection or immune disfunction.

In another aspect, this invention can provide a treated donor organ or tissue for transplantation comprising the organ or tissue in combination with the dimeric material.

DETAILED DESCRIPTION OF THE INVENTION

The Dimeric Concanavalin A

The present invention employs dimers of concanavalin A. These materials are referred to generically as CAD, or Concanavalin A Dimers. One form of dimeric CA is the native dimer having a molecular weight of about 52–53,000. This material can be obtained by adjusting the pH of a purified solution of CA to below about 6.0, such as in the range of pH 4 to pH 6, thereby disassociating any CA tetramer or higher aggregates into the desired "dimer" form. Such solutions are stable at pH's up to about 6.3 at temperatures of from below freezing to about 30° C. Preferred solutions of the native dimer have pH's of form about 4.5 to about 6.0 and are stored for long periods at temperatures below about 10° C. These native dimer materials are characterized by containing at least about 80% of their total CA as the dimer form. These materials and methods for their preparation are described in Huet, *BIOCHEM.* 59 627–632 (1975) and McKenzie, et al., *BIOHEM. BIOPHYS. ACTA.* 263, 283–293 (1972). A preparation of this native dimer material which is preferred because of the pure and exceptionally stable product which it provides is described by A. Sophianopoulos, et al in *PREP. BIOCHEM.*, 11 (4), 413–435. These papers describe in more detail the factors which favor dimer in a solution of CA. These papers are incorporated herein for reference.

The other "dimeric" materials useful in this invention are chemically-modified CA's which have a dimeric structure. These materials include the reaction product of CA with succinic anhydride to yield a succinylated CA or "SCA", and the reaction product of CA with acetic anhydride to yield acetylated CA or "ACA" and the reaction product of CA with maleic anhydride to yield maleited CA or MCA. Typical preparations of these materials are provided in the paper of Gunther, G. R., et al., *PROC. NAT. ACAD. SCI., USA*, 70, No. 4, 1012–1016 (April 1973) which is incorporated herein by reference. Additional representative dimer materials include the hybrid dimers made up as a hybrid of native CA "monomer" and a SCA, ACA or the like "monomer." Such materials are described in Fraser, et al. *J. BIOL. CHEM.*, 251, No. 15, 4622–4628 (Aug. 10, 1976), which is incorporated herein by reference. An additional group of useful dimers are the "cross-linked dimers" formed by reacting CA with SCA, ACA or MCA in the presence of a bifunctional coupling reagent such as a diisocyanate, in particular a lower alkaline diisocyanate such as hexamethylene diisocyanate. Such materials are described in Wang. et al. *J. BIOL CHEM.*, 253, No. 9, 3000–3007, (May 10, 1978) which also is incorporated herein by reference.

All of these materials are characterized by comprising two of the saccharide-binding subunits, each of molecular weight of about 26,000 so as to give rise to a dimer molecular weight of about 52,000–53,000.

The invention is not limited to the particular dimeric materials just related and can employ other chemically modified CA substrates so long as the overall structure of the predominant material (i.e. 60% or more, preferably 80% or more, and more preferably 90% or more of the total CA) is of a dimeric structure. Mixtures of two or more dimeric materials can be used, if desired.

Pharmaceutical Preparations

The dimeric CA material is formulated into a pharmaceutical preparation, generally for parenteral administration (i.e. I.V. or intramuscular injection) but also for oral administration. In parenteral administration, the preparation can be administered I.V. or I.M. over a prolonged period or by periodic injections.

Suitable preparations are composed of one or more of the dimers in association with a pharmaceutically acceptable carrier. The book, *REMINGTON'S PHARMACEUTICAL SCIENCES*, 15th Ed., E. W. Martin, (Mack Publ. Co., 1975), discloses typical carriers and methods of preparation. This disclosure is incorporated herein by reference. Typical carriers include injectable saline, injectable water and injectable solutions, with or without buffers, isotonicity agents and the like.

The injectable compositions contain from about 0.005% to about 20% of the dimer, preferably from about 0.01% to about 10% of the dimer, and more preferably 0.1% to 5%. Oral compositions can vary over a wider range so long as the volume of composition needed to deliver an effective dose is reasonable for a patient to consume.

The materials of this invention find use as immunomodulators. They can thus be used to ameliorate the effects of undesired immune system reaction such as observed in organ and tissue graft rejection as well as to treat immune disfunction conditions such as autoimmune disease states—i.e. lupus, diabetes, arthritis, ulcerative colitis, acquired immune deficiency syndrome, multiple sclerosis and the like.

The dimers and compositions containing them can be administered in a variety of ways. In tissue and organ rejection settings they can serve to prevent rejection. This can be carried out by treatment of the organ or tissue prior to implantation in the recipient or by administering the dimers to the recipient prior to concurrent with or and/or after the transplantation. To treat rejection episodes, administration of the dimer can be initiated or augmented at the time rejection is suspected or diagnosed.

These treatments can be carried out with the CAD alone or accompanied by other therapeutic strategies such as immunoregulatory drugs for example steroids, antimetabolites, cyclosporines, lymphokines or other natural products or the like. In addition, these materials can work with donor antigens in the form of blood, blood components, particulated blood antigens and the like, if desired.

In autoimmune disease settings, the CAD materials serve to treat the disease caused by autoimmunity by regulating the immune process. This can be carried out by subjecting the patient to a regimen of treatment consistent with the course of the disease. The treatment can halt the progression of the disease or reverse damage already done by the disease. As in the case of tissue or organ rejection, treatment, the CAD can be used alone or in conjunction with other therapeutic strategies.

As will be apparent from the above, the CAD materials can be administered over a wide range of schedules and doses. In the case of graft or transplant rejection, dosage can begin prior to or simultaneous with or after the graft or transplant is carried out. Typically, the treatment can begin from weeks before to a week after the graft or transplant and continue for up to a year or more up to the lifetime of the patient.

In the case of the immune disfunction states, typical courses of treatment can run from the time the disease is diagnosed or suspected and is continued until the disease is arrested or reversed. Such times can range from a single dosing to virtual lifetime treatment.

Typical dose levels are from 0.1 mg/kg/day to 500 mg/kg/day with dose levels of from 0.25 mg/kg/day to 200 mg/kg/day being preferred and with dose levels of from 0.50 mg/kg/day to 100 mg/kg/day being more preferred.

This invention will be further described by reference to the following examples. These are provided solely to illustrate modes of practicing the invention and are not to be construed as limiting the scope of the invention which is, instead, defined by the appended claims.

EXAMPLE 1

This example illustrates the ability of a therapeutic composition based on the CA dimer, succinylated CA, to reduce graft and transplant rejection in a mammal animal model. The compositions of the invention prolong survival of the treated animals after heart transplantation.

A composition of the invention is prepared from SCA. The SCA is purchased as lyophilized powder from Vector Labs, dissolved to 10 mg/ml in 0.9%w normal saline and stored at 4° C. Analysis of the SCA (as well as native CA purchased from the same source and made up into an identical strength solution) by isoelectric focusing on preformed polyacrylamide gel plates shows that the SCA migrates as a single band whereas CA is composed of four components migrating with pIs near neutrality. These results indicate that the SCA employed is composed essentially completely of the desired dimer.

Male Lewis (LEW, $RT1^l$), Brown Norway (BN, $RT1^n$) and Lewis×Brown Norway $F_1$, hybrid (LBN) rats weighing between 220-350 gm are obtained from Charles Rivers or Harlan Sprague Dawley. Donor whole hearts are transplanted by primary vascular anastomosis in the heterotopic (abdominal) position. LEW recipients of LBN or BN hearts are treated I.V. with either saline (control) or SCA beginning two days before surgery and continued on a daily basis until the day of rejection.

Hearts are palpitated daily for the presence of contractile activity. The day on which all contractile activity stopped is defined as the day of rejection.

The in vivo activities of SCA is evaluated by determining this dimer's ability to prevent cardiac allograft rejection. LBN hearts in untreated LEW rats survived for 2×8, 9, 12, 14 and 15 days. SCA treatment at doses of 3 mg/kg and 15 mg/kg cause grafts to survive 12 and 13 days and 20, 25, 29, and 34 days, respectively.

None of the recipients treated with SCA at any dose shown any signs of overt, clincial toxicity at any time. After three weeks of treatment with 15 mg/kg of SCA, the recipients' total white blood cell count is normal. A dose of 6 mg/kg of CA causes a 40% reduction in the WBC during the third week of treatment.

EXAMPLE 2

The materials of this invention are used to control rejection in the clinic in the following way. A living related or cadaver kidney donor is identified. In the case of the living related donor, blood from the living related donor is transfused into the recipient weekly for six weeks prior to transplantation. In the case of the cadaver donor, ABO compatible random blood transfusions are given according to a similar schedule. During this time CAD (for example 10 mg for SCA/kg/day, I.V.) optionally with other immunosuppressive strategies (e.g., drugs like prednisone, or X-irradiation) is also given. Six days I.V. (in the case of the living related donor transplant, or 12 hours (in the case of the cadaver donor transplant) before surgery, CAD is given to the prospective recipient at a dose level of 10 mg/kg.

The donor organ is removed from the donor and perfused with a solution of electrolyte containing 0.5 mg/ml CAD for 10 minutes for 2 days before implantation into the recipient.

In the post operative period, CAD treatment is continued at 10 mg/kg/day, I.V., to prevent the onset of rejection. The CAD is used in conjunction with other immunoregulatory strategies, such as immunosuppressive drugs like cyclosporine and the like. If organ rejection is suspected, or diagnosed, the amounts of CAD and other immunoregulatory drugs are increased until the rejection process is altered, or preferably, reversed.

EXAMPLE 3

The Experiments of Example 1 are repeated with the change that in place of SCA, and equivalent amount of acetylated CA (ACA) is employed. Similar results would be observed.

EXAMPLE 4

The Experiments of Example 1 are repeated with the change that in place of SCA, and equivalent amount of isolated dimeric native CA prepared by the method of Sophianopoulos, et al in PREP. BIOCHEM., 11 (4), 413–435. If this material is tested by isoelectric focusing it would be observed to be over 80% of the desired dimeric material. Similar in vivo test results would be observed.

What is claimed is:

1. A method of inducing immunoregulation in a mammal in need of immunoregulation comprising administering to such mammal an effective immunoregulatory amount of homogeneous concanavalin A dimer in a pharmaceutically acceptable carrier.

2. A method of inducing immunoregulation in a mammal in need of immunoregulation comprising administering to such mammal an effective immunoregulatory amount of an at least 80% homogeneous concanavalin A in a pharmaceutically acceptable carrier.

3. The method of inducing immunoregulation in a mammal in need of immunoregulation of claim 2 wherein the concanavalin A dimer comprises native concanavalin A dimer.

4. The method of inducing immunoregulation in a mammal in need of immunoregulation of claim 2 wherein the concanavalin A dimer comprises succinylated concanavalin A dimer.

5. A treated donor organ for transplantation comprising the organ in combination with a pharmaceutical preparation comprising an effective amount of homogeneous concanavalin A dimer.

6. A treated donor tissue for transplantation comprising the tissue in combination with a pharmaceutical preparation comprising an effective amount of homogeneous concanavalin A dimer.

7. The method of inducing immunoregulation in a mammal in need of immunoregulation of claim 2 wherein the concanavalin A dimer comprises acetylated concanavalin A dimer.

8. The method of inducing immunoregulation in a mammal in need of immunoregulation of claim 2 wherein the immunoregulation comprises immunosuppression.

9. The method of inducing immunoregulation in a mammal in need of immunoregulation of claim 4 wherein the immunoregulation comprises immunosuppression.

* * * * *